United States Patent [19]

Groh

[11] Patent Number: 5,343,536
[45] Date of Patent: Aug. 30, 1994

[54] METHOD OF USING IMAGE ANALYSIS UNDER CROSS-POLARIZED LIGHT TO EVALUATE FOLLICULAR BIOPSY SLIDES

[75] Inventor: David G. Groh, Grand Rapids, Mich.

[73] Assignee: Amway Corporation, Ada, Mich.

[21] Appl. No.: 979,700

[22] Filed: Nov. 20, 1992

[51] Int. Cl.$^5$ .............................................. G06K 9/00
[52] U.S. Cl. .................... 382/6; 364/413.1; 382/54
[58] Field of Search ..................... 382/6, 4, 54; 424/728.03, 448; 514/844; 364/413.13, 413.1

[56] References Cited

U.S. PATENT DOCUMENTS

| | | | |
|---|---|---|---|
| 4,207,554 | 6/1980 | Resnick et al. | 382/6 |
| 4,637,053 | 1/1987 | Schalkowsky | 382/6 |
| 4,724,215 | 2/1988 | Farber et al. | 356/419 |
| 4,741,043 | 4/1988 | Bacus | 382/6 |
| 4,752,472 | 6/1988 | Kligman | 424/81 |
| 4,847,910 | 7/1989 | Sakuraba et al. | 382/6 |
| 4,856,073 | 8/1989 | Farber et al. | 382/6 |
| 4,932,044 | 6/1990 | William et al. | 382/6 |
| 5,107,422 | 4/1992 | Kamentsky et al. | 382/6 |
| 5,123,055 | 6/1992 | Kasdan | 382/6 |
| 5,163,095 | 11/1992 | Kosaka | 382/6 |

OTHER PUBLICATIONS

Analysis of Facial Comedos by Porphyrin Fluorescence and Image, by G. Sauermann, Ph.D., B. Ebens, Ph.D. and U. Hoppe, Ph.D.

Polarized Light Examination and Photography of the Skin, by R. Rox Anderson, M.D.

*Primary Examiner*—Joseph Mancuso
*Attorney, Agent, or Firm*—Michael A. Mohr; Jill M. Beckman

[57] ABSTRACT

A method of evaluating follicular biopsy specimens (skin samples) in order to count the number of comedones (25) present in the specimen involving the steps of applying an adhesive, in vivo, to a subject's skin; applying a microscopic slide to the adhesive covered skin; allowing the adhesive to set adhering to the slide; removing the slide with the adhesive and the skin attached thereto, thus yielding a follicular biopsy specimen; examining the specimen under a stereoscopic microscope under cross-polarized light then evaluating the specimen using image analysis hardware and software to determine the number of sebaceous plugs or comedones existing in the specimen.

10 Claims, 6 Drawing Sheets

METHOD OF USING IMAGE ANALYSIS UNDER CROSS-POLARIZED LIGHT TO EVALUATE FOLLICULAR BIOPSY SLIDES

FIELD OF THE INVENTION

The present invention relates generally to a method for evaluating comedones on the skin through the use of follicular biopsy slides and image analysis. More particularly, the present invention relates to a method for evaluating and counting the number of comedones (a collection of sebaceous material and carotin retained in the hair follicle and excretory ducts of the sebaceous glands commonly known as blackheads) occurring on a skin sample taken from a human subject using image analysis software to evaluate a digitized image taken of the skin sample through a stereoscopic microscope under cross-polarized light. Such evaluations are useful to provide important data in the testing of new and existing cosmetics and skin products to determine whether such products are comedogenic to human skin.

BACKGROUND OF THE INVENTION

Comedogenic products clog pores and follicles and inhibit the skin's natural cleansing of sebaceous materials. Sebaceous materials found in the skin are composed of fats, cellular debris and keratin. These sebaceous materials, if trapped within pores or follicles, become a site for the growth of corynebacterium acnes. In a short time these sites also accumulate dirt causing the pore or follicle to become a blackhead or comedone. Such comedones, over time, may become infected and contribute to the onset of acne.

The use of image analysis in conjunction with UV light to evaluate facial comedones is known and is described in *Analysis of Facial Comedos by Porphyrin Fluorescence and Image Analysis* by G. Sauermann, Ph.D, B. Ebens, Ph.D and U. Hoppe, Ph.D. Porphyrin, which is a class of red pigmented compounds which form the active nucleus of hemoglobin in blood, are synthesized by corynebacterium acnes and are present in the material composing the comedones. The porphyrins fluoresce under ultraviolet light causing the comedones to glow so that they can be either manually counted or analyzed by the use of image analysis software. However, the use of porphyrin fluorescence under UV light has a number of drawbacks: The porphyrin synthesized by the corynebacterium acnes present in the sebaceous glands will fluoresce under UV light only while the bacteria is actively synthesizing porphyrin. Thus, the most reliable UV testing method is to shine the ultraviolet light directly on the subject's skin, in vivo, in order to cause the porphyrins to fluoresce so that the number of comedones on the skin area being analyzed can be more easily seen and counted. However, it is well-known that ultraviolet light emits radiation and overexposure can be hazardous to the skin of the subject as well as to the retinas of the scientist conducting the analysis. Further, using the same UV method upon a removed skin sample is unreliable due to the fact that the corynebacterium acnes only synthesize porphyrins for a very short time in dying skin giving erratic and erroneous comedone counts because porphyrins fluoresce only during synthesis. Another drawback is that not all comedones contain porphyrin which, therefore, would not fluoresce under the UV light resulting in an erroneous comedone count.

Prior to the use of image analysis, follicular biopsy samples were evaluated manually under a stereo microscope. The comedones were counted, sized and each were assigned a number grade global evaluation to the follicular biopsy sample. Global evaluations were based on a standard four-point scale with zero being non-comedogenic and three being comedogenic. However, manual evaluation of follicular biopsy samples is very slow, painstaking and tedious and there may be large differences between evaluation of the same sample depending upon the scientist performing the evaluation.

SUMMARY OF THE INVENTION

These problems and others are solved by provision of a unique method of using image analysis to automatically evaluate follicular biopsy slides through the use of a personal computer, a high resolution video monitor, image analysis software and a stereoscopic zoom microscope provided with a source of cross-polarized light.

In preparation for the follicular biopsy evaluation method of the present invention, a number of test areas are mapped out above the scapulae or shoulder blades of a live human subject, usually by drawing a square or encircling a predetermined number of areas on the skin using a cosmetic pencil or the like. Each area mapped out on the subject should be generally 25 square centimeters in size or of sufficient size to apply a test substance or a product to be tested upon the skin of the subject. Generally, in a controlled experiment, one or more sites are left untreated while the other sites have the test substance applied thereto. In a test area, test substances are liberally applied to the skin enclosed in each square or circle. An occlusive or gas permeable tape may be applied to protect and secure the test area during the evaluation period which varies depending upon the substance being tested.

According to the method of the present invention, skin samples are taken from the test area by first applying a film of adhesive to the skin in the test area then applying a glass microscopic slide to the film of adhesive and allowing the adhesive to set with the slide adhered thereto. Next, after the adhesive is set, usually only after a few seconds, the slide is manually removed taking along with it a thin layer of skin containing comedones and other materials of the skin attached thereto from the subject test area, thereby yielding a skin specimen. The skin specimen will provide a negative relief of the skin with the comedones and other materials taken from the skin test area appearing as raised areas from the skin itself adhered to the slide. Next, the scientist will place the microscopic slide with the skin specimen under a stereoscopic microscope and examine it using a ring light adapted to provide cross-polarized light.

Using cross-polarized light to view the skin sample is highly desirable because when the planes of polarization are adjusted properly, raised structures on the negative skin sample such as comedones and other materials pulled from within the skin of the subject can be sharply focused in contrast to the less prominent surface features of the skin sample without blurring or taking the remainder of the skin sample out of focus. Thus, when adjusted properly under the cross-polarized light, the comedones will appear as glowing areas against the backdrop of a darker skin surface. Therefore, with the comedones appearing as bright, highly defined objects under the cross-polarized light, a digital image analysis apparatus will scan and capture an image of the specimen, digitize it and the computer will then store the digitized image as binary data. Image analysis software is then used to evaluate the digitized image automatically using a machine-readable task list programmed by the scientist which preferably will define which objects to evaluate on the sample and what measurements the image analysis system should record. The image analysis program will then automatically record and store the appropriate data from each sample. The stored data can be accessed at a later date using the image analysis software which will perform an analysis of the sample data under user-defined parameters set forth in the machinereadable task list. The task list created by the scientist for the evaluation of the sample will automatically evaluate the number of objects, object area, object length, object perimeter, object circularity and total detected area of the skin sample. Simply put, the task list is a machine-readable instruction program that defines which objects on the skin sample the image analysis system will evaluate and what measurements it should record. Thus, such image analysis evaluation will yield a summary of results giving an average number of comedones per sample. In fact, it was determined that there is a high degree of correlation between the results achieved by manual evaluation of follicular biopsy samples using the UV method on living skin and results achieved using the method of the present invention. Such high degree of correlation was found to be at the 95% confidence level between test results proving that the method of the present invention is as accurate as the more tedious UV method discussed above yet is much safer, much faster and is not subject to result variations.

DETAILED DESCRIPTION OF THE PREFERRED EMBODIMENT

Figure 1:
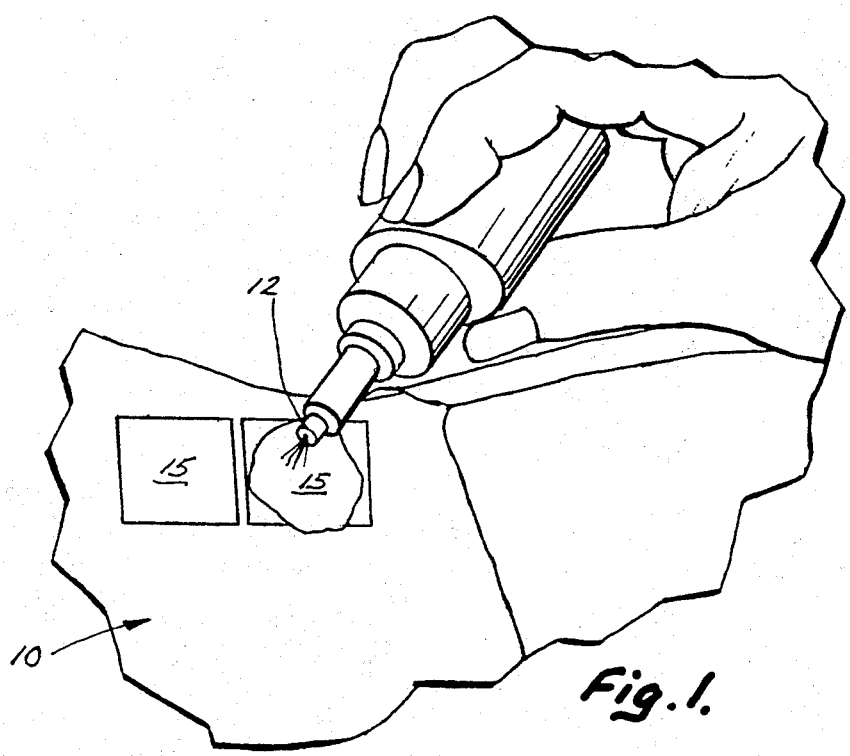
FIG. 1 shows in the method of using image analysis under polarized light to evaluate follicular biopsy slides the step of applying a film of adhesive to the skin of a subject within a test area mapped above the subject's scapulae.

With reference to the figures, and particularly FIG. 1, a test subject is shown generally at 10 having test areas 15 mapped out upon the skin thereof just above the scapulae. One test area 15 is shown to be defined by a square drawn around an area of approximately 25 square centimeters.

Figure 2:
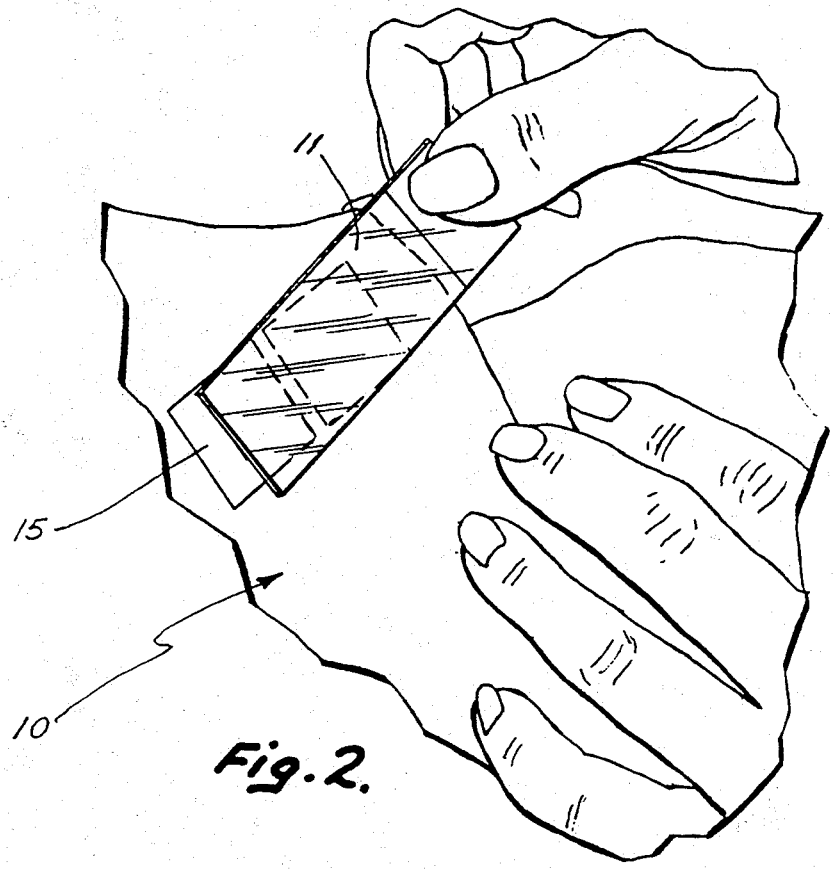
FIG. 2 shows the method step of applying a microscopic slide to the adhesive thereof.
Figure 3:
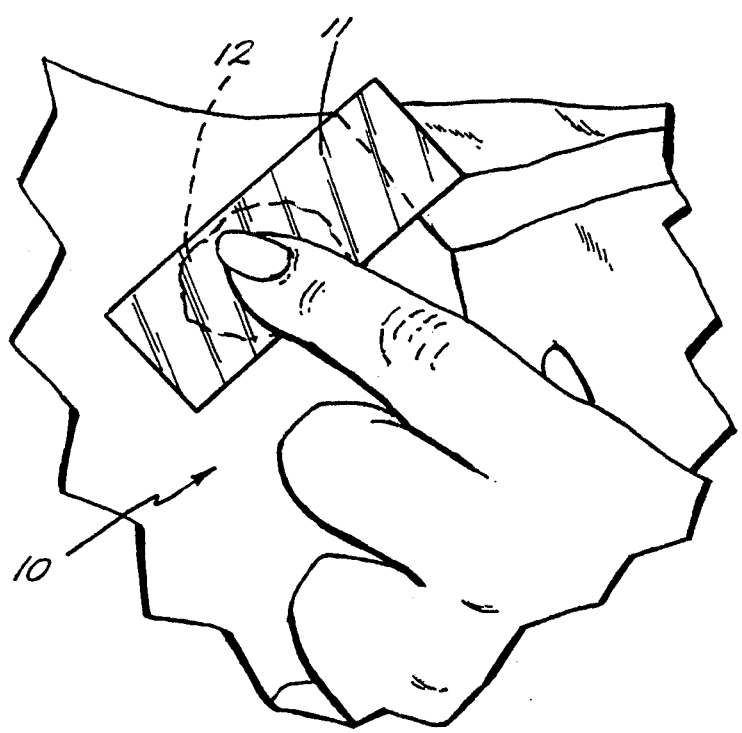
FIG. 3 shows the method step of holding the microscopic slide in place while the adhesive sets thereof.

A film of an adhesive 12 is applied to the test area 15 and, with reference to FIG. 2, a microscopic slide 11 is placed thereon while the adhesive 12 has not yet fixated. With reference now to FIG. 3 with slide 11 in place, it is held until adhesive 12 fixates or sets, usually within a few seconds. Setting time may vary depending on the type of adhesive used with the most preferred adhesive being a liquid polymerizable cyanoacrylate adhesive commonly marketed under the brand names Krazy Glue, Super Glue and Loctight. The material of the microscopic slide 11 is preferably a material that is non-reactive to cyanoacrylate, and is most preferably glass as glass slides tend to be more durable than thinner, film slides.

Figure 4:
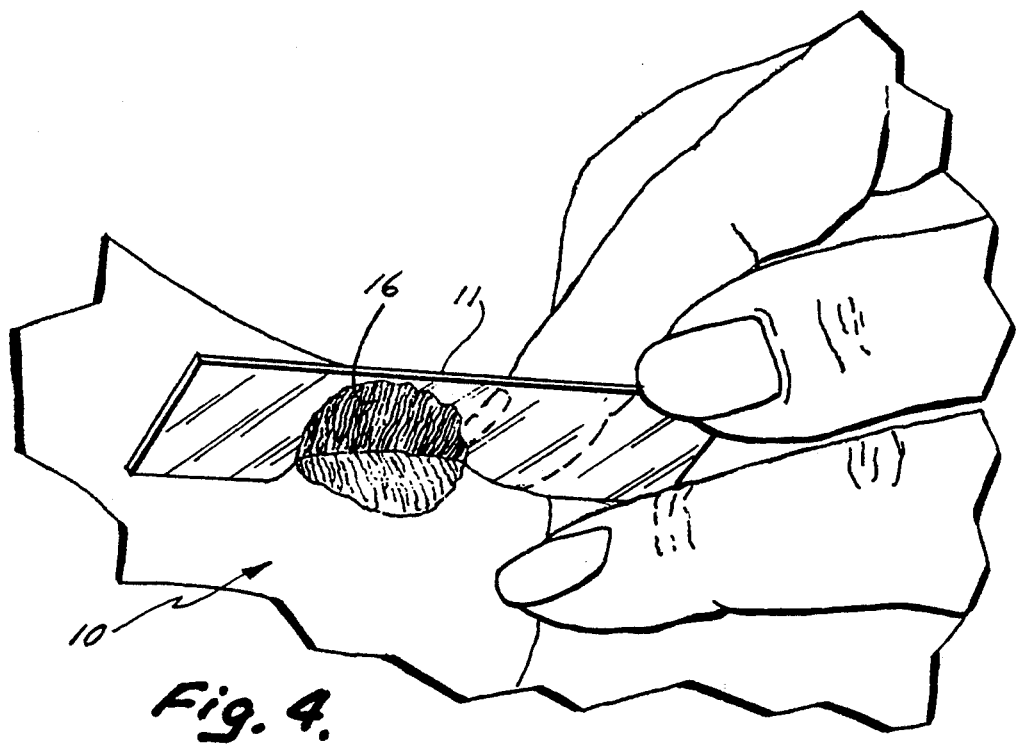
FIG. 4 shows the method step of removing the slide and the adhesive film along with the skin sample attached thereto.
Figure 5:
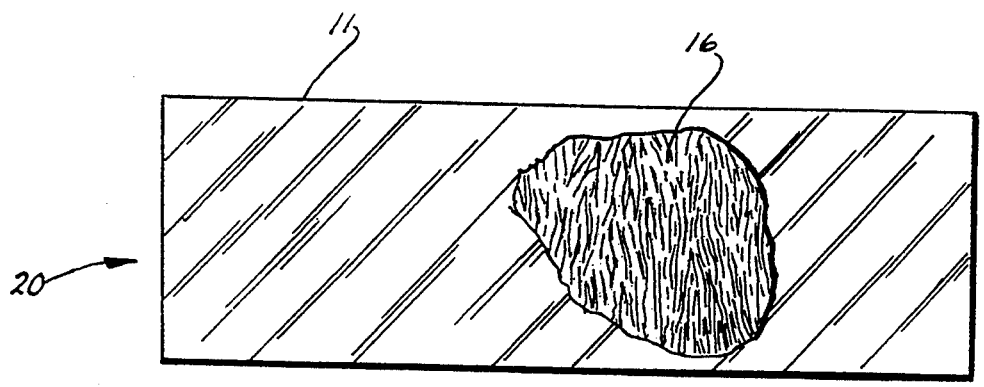
FIG. 5 shows the resulting skin sample upon the microscopic slide.
Figure 6:
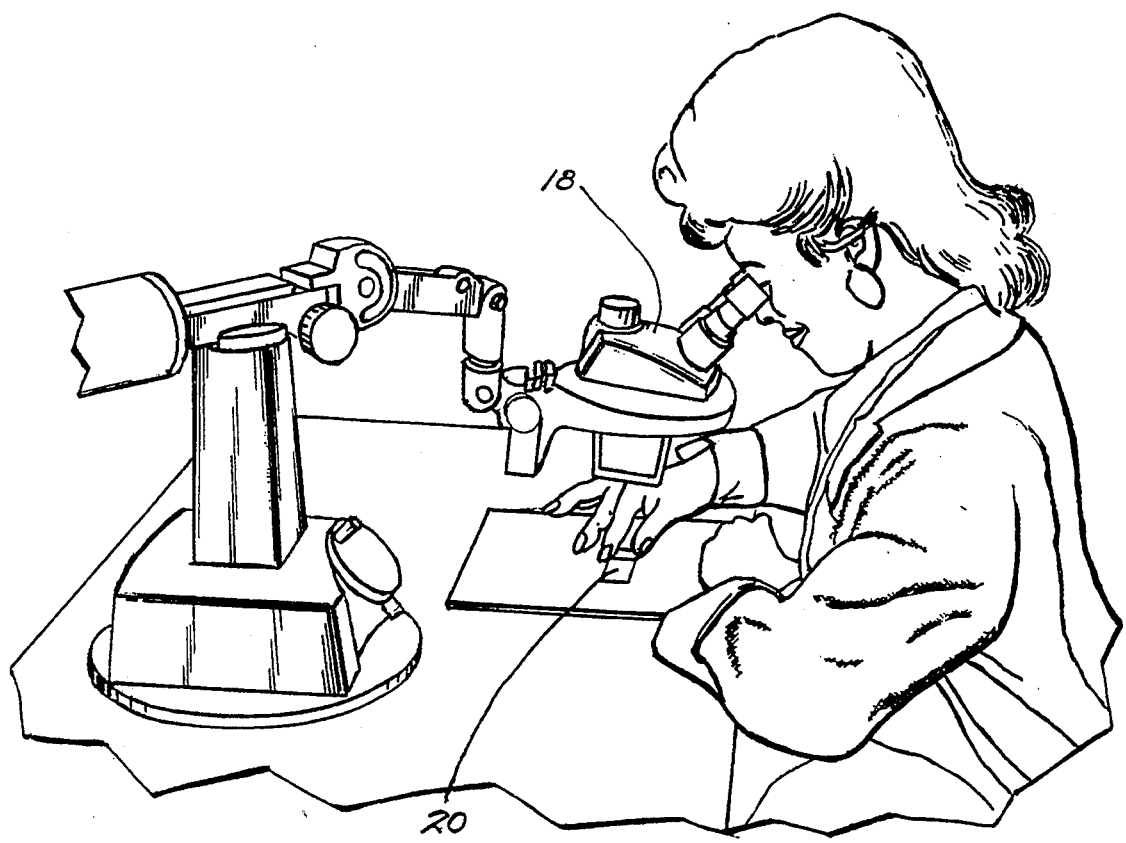
FIG. 6 shows the method step of examining the skin sample under a compound stereoscopic microscope.

With reference now to FIG. 4, after the adhesive 12 has properly set, the slide 11 is manually removed by lifting slide 11 away from the skin taking with it a skin sample 16 from test area 15 yielding a follicular biopsy sample more clearly shown in FIG. 5 generally at 20. Referencing also FIG. 6, the follicular biopsy sample 20 is placed under a compound stereoscopic microscope 18 and is examined under cross-polarized light at a magnification of 15X. A magnification of 15X is most preferred given the size of the objects appearing on the follicular biopsy sample 20. A greater or lesser magnification is less desirable yet may be used. For purposes of the following disclosure, a magnification of 15X is assumed. Any compound microscope may be utilized for the method of the present invention but a compound stereoscopic microscope is preferred, primarily for the benefit of the scientist viewing the follicular biopsy sample 20.

Figure 7:
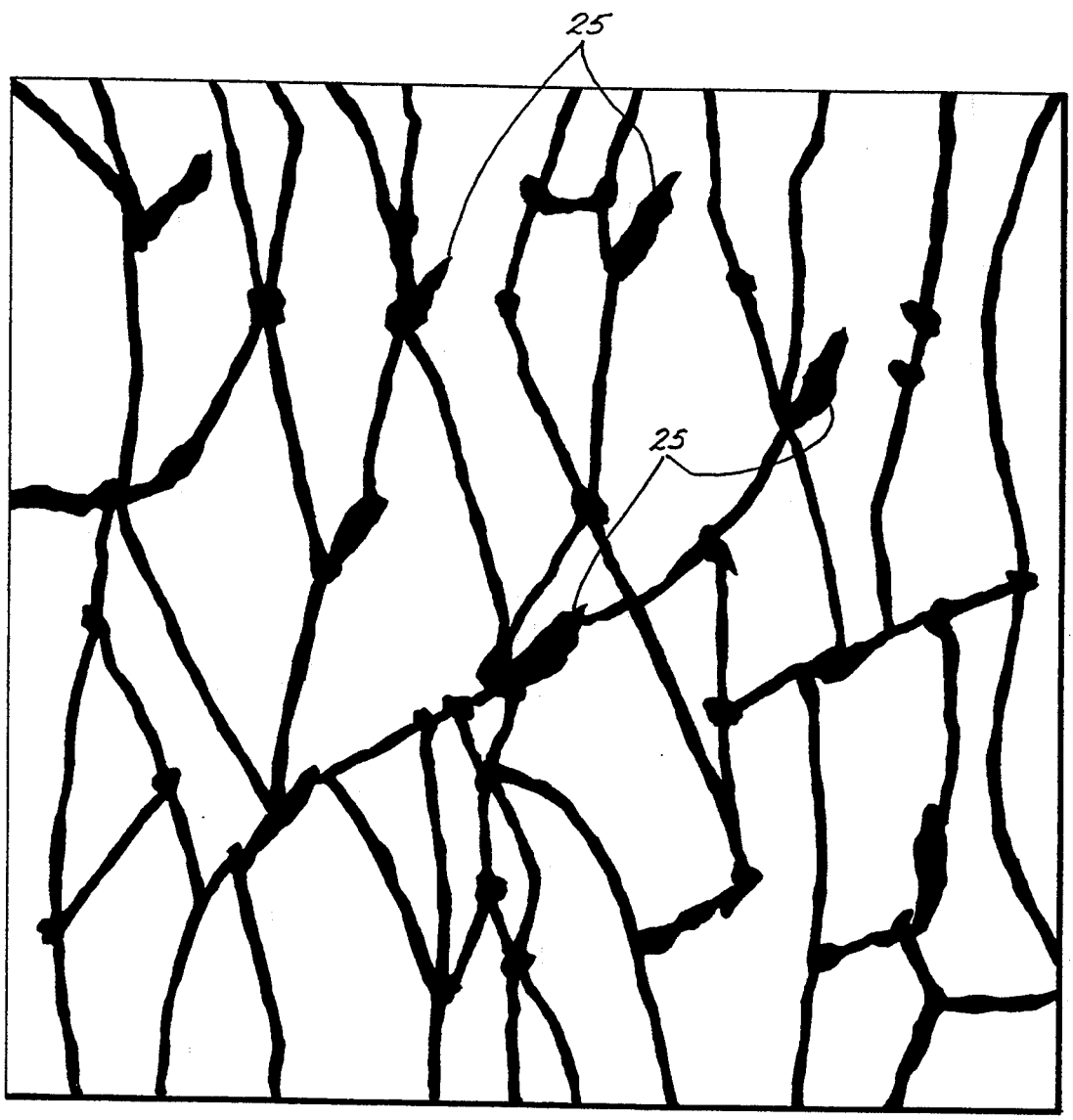
FIG. 7 shows the skin sample as it would appear under the compound stereoscopic microscope using natural light.
Figure 8:
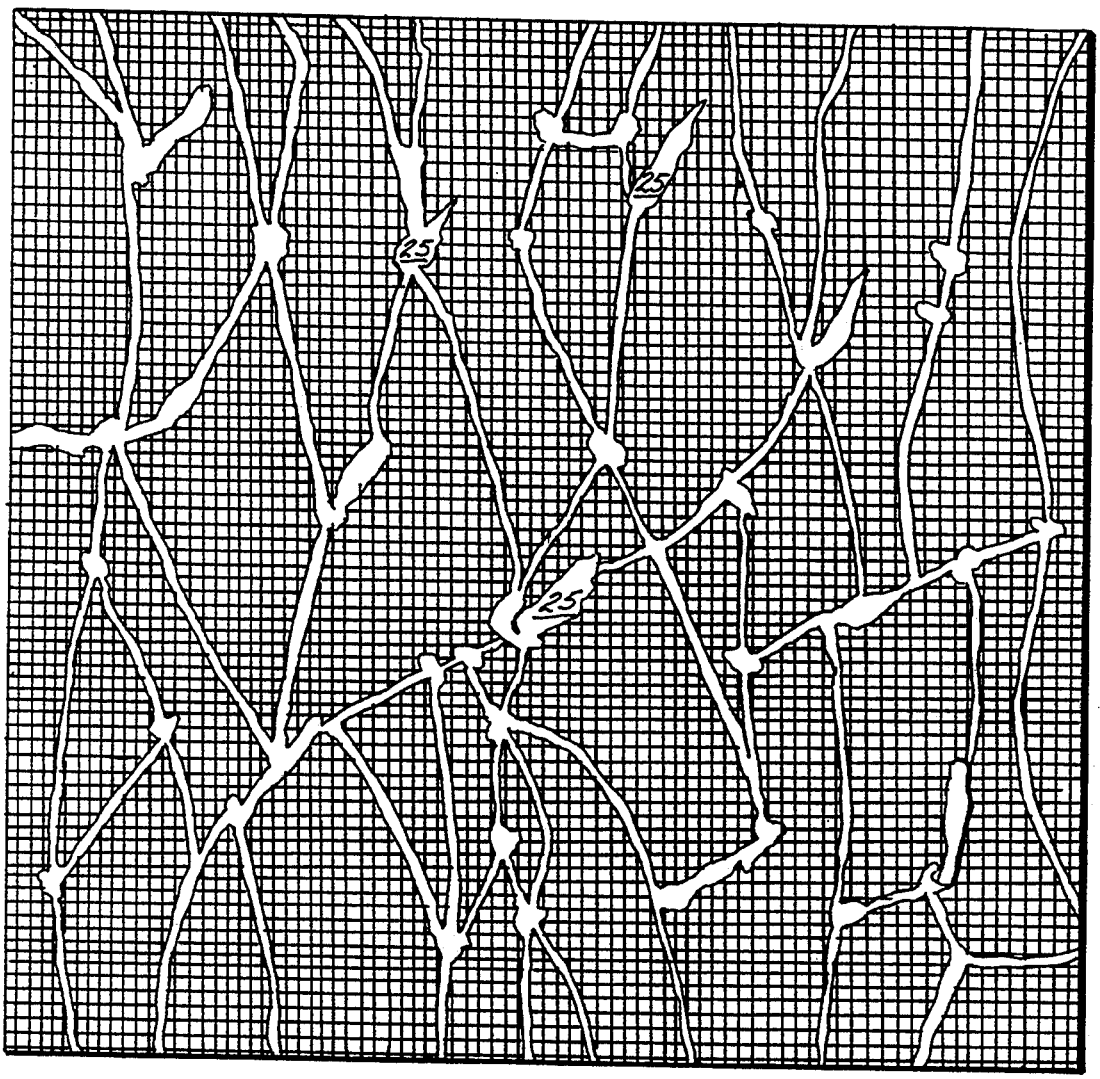
FIG. 8 shows the skin sample as it would appear under the compound stereoscopic microscope using cross-polarized light with the comedones appearing as bright areas against a darker background.

With reference to FIG. 7, follicular biopsy sample 20 is shown as it appears under compound stereoscopic microscope 18 under natural light. FIG. 8 shows a follicular biopsy sample as it appears under compound stereoscopic microscope 18 under cross-polarized light. In FIG. 7, follicular biopsy sample 20 under natural light shows significant surface glare with comedones 25 and other sebaceous materials appearing as slightly darker areas not easily distinguishable from surrounding glare and shadows caused by the refracting natural or ambient light. However, the follicular biopsy sample 20 shown in FIG. 8 under cross-polarized light contains no glare and shows comedones 25 and other sebaceous materials appearing as bright areas clearly distinguishable against a darker skin surface background.

Figure 9:
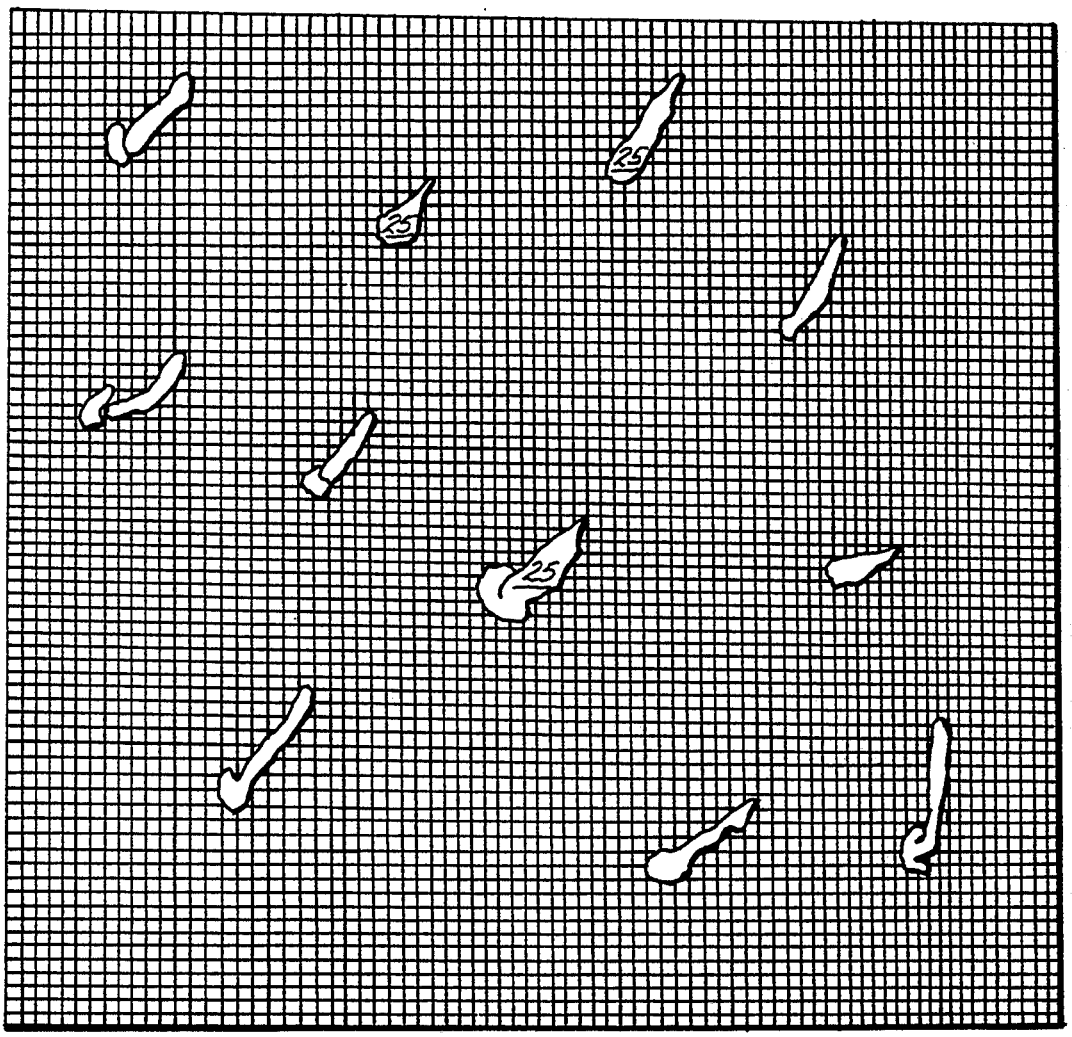
FIG. 9 is a binary image of the skin sample of FIG. 8 captured using image analysis hardware and software.

Using image analysis hardware and software, the follicular biopsy sample 20 of FIG. 8 is scanned and captured as a binary image 30 shown in FIG. 9. However, the way in which the hardware and software capture the image and store it is determined by a machine-readable task list written by the evaluating scientist according to the nomenclature of the particular image analysis software used. The preferred image analysis hardware and software for the present invention is manufactured by Joyce-Loebl Limited and is sold under the trademark MINI-MAGISCAN. The software, which is a part of the Joyce-Loebl Limited MINI-MAGISCAN package, is sold under the trademark GENIAS25 Version 2.1. However, many other image analysis hardware and software packages may be substituted and configured to achieve the same results.

The task list created by the scientist for use with the image analysis software provides specialized instructions to the image analysis hardware as to what areas of the follicular biopsy sample to evaluate. First, the task list instructs the image analysis hardware to apply a value to the background lighting on the stereoscopic microscope stage before the image is captured. Such lighting would include not only the cross-polarized light radiating from the circular polarized light ring but also any ambient light in the room or any shadows cast therefrom. Next, the task list instructs the image analysis hardware to capture a binary image of follicular biopsy sample 20. The captured binary image is a matrix of pixels or picture elements. While capturing the binary image, the image analysis hardware will subtract or filter out light that equals the value the software applied to the background light upon the stage of microscope 18. Further, if any objects appear in the scanned image as brighter than the background light, such as a hair which appears very bright under cross-polarized light, the image analysis system will also subtract its value from the image. This is done by taking the mean average of the intensity of pixels neighboring any irregular object appearing on the specimen and applying that value to the pixels of the irregular object, thus diminishing the object to appear as part of the background.

A normal image captured by image analysis software is composed of 64 different grey levels whereby a zero level will appear as black and 63 and above will appear as bright white. In order to create a binary image the task list used in the present invention will instruct the image analysis system to look at only the grey levels that fall between 50 and 63 and to ignore anything falling outside those parameters in order to distinguish comedones from other objects such as hair, which appears bright under cross-polarized light, and background objects which are darker than the comedones. Thus, a binary image is created by the image analysis software whereby all grey level objects having a value between 50 and 63 are considered to be in an "on" state and all grey level values of 50 and below and 63 and above are considered to be in an "off" state. The images between the levels of 50 and 63 that have been turned "on" are the comedones 25 of follicular biopsy sample 20 which appear as red dots against a dark background represented in FIG. 9 (not shown in red). The task list will then instruct the image analysis system to delete or turn "off" clusters of pixels in the image that are between zero and ten pixels in size. Comedone-sized clusters will be the largest objects on follicular biopsy sample 20 and generally comprise clusters made up of more than 10 pixels at the preferred magnification of 15X. As mentioned earlier, a greater or lesser magnification may be used provided that the task list is modified to instruct the image analysis system to look for larger or smaller clusters of pixels respectively. However, deviating from the preferred magnification of 15X is undesirable due to the similarities in comedone size from specimen to specimen whereby the 15X magnification has the best field of vision encompassing all or most of specimen 20.

Lastly, the task list instructs the image analysis system to measure the comedones 25 (comedone-sized clusters) appearing in the binary image 30 of follicular biopsy sample 20 for size and shape and count the total number of comedones 25 appearing in the image 30 after which the program ends.

It is essential to the operation of the image analysis software using the above-described task list to evaluate comedones that a cross-polarized light is used. Otherwise, the contrast of the comedones to other objects as demonstrated in FIG. 7 will not be sufficient for the image analysis system to segregate the desired objects from undesirable objects.

An example of the original task list used in the method of the present invention with the Joyce-Loebl Limited MINI-MAGISCAN system and the GENIAS25 Version 2.1 software is provided below as Table 1.

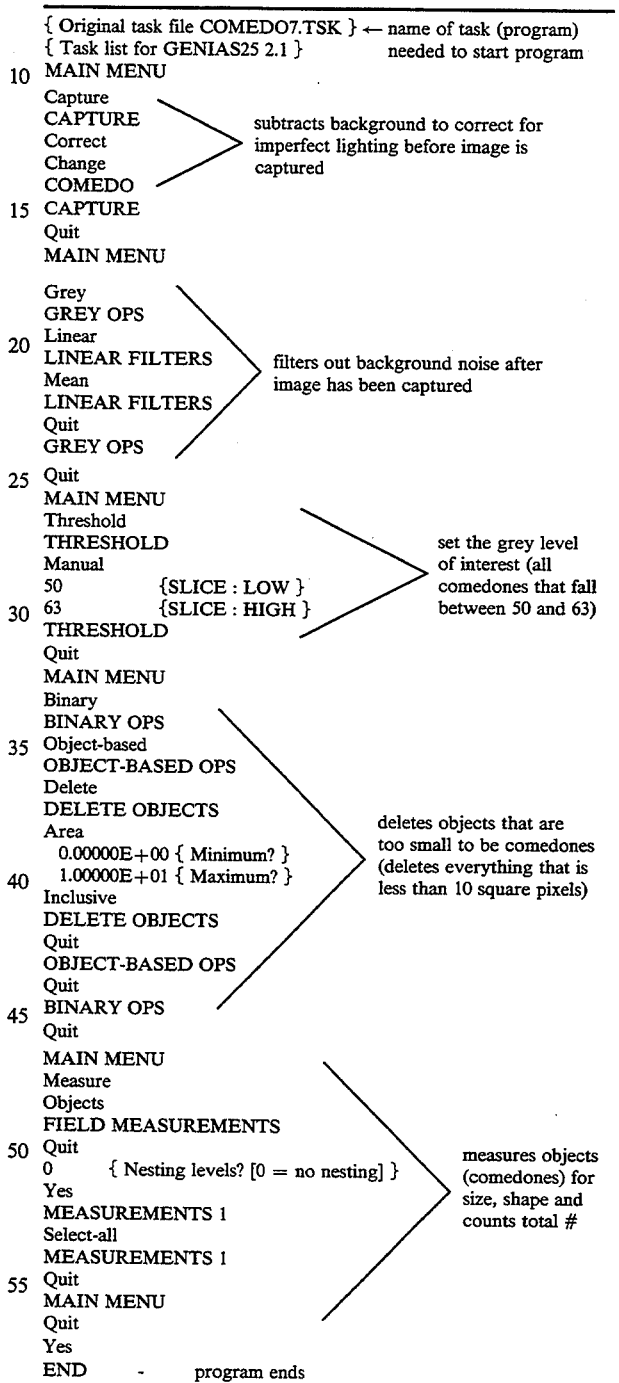

```
{ Original task file COMEDO7.TSK }  ← name of task (program)
{ Task list for GENIAS25 2.1 }          needed to start program
MAIN MENU
Capture
CAPTURE                                  subtracts background to correct for
Correct                                  imperfect lighting before image is
Change                                   captured
COMEDO
CAPTURE
Quit
MAIN MENU
Grey
GREY OPS
Linear
LINEAR FILTERS              filters out background noise after
Mean                        image has been captured
LINEAR FILTERS
Quit
GREY OPS
Quit
MAIN MENU
Threshold
THRESHOLD                                set the grey level
Manual                                   of interest (all
50          {SLICE : LOW }               comedones that fall
63          {SLICE : HIGH }              between 50 and 63)
THRESHOLD
Quit
MAIN MENU
Binary
BINARY OPS
Object-based
OBJECT-BASED OPS
Delete
DELETE OBJECTS
Area                                     deletes objects that are
   0.00000E+00 { Minimum? }              too small to be comedones
   1.00000E+01 { Maximum? }              (deletes everything that is
Inclusive                                less than 10 square pixels)
DELETE OBJECTS
Quit
OBJECT-BASED OPS
Quit
BINARY OPS
Quit
MAIN MENU
Measure
Objects
FIELD MEASUREMENTS
Quit                                     measures objects
0      { Nesting levels? [0 = no nesting] }   (comedones) for
Yes                                      size, shape and
MEASUREMENTS 1                           counts total #
Select-all
MEASUREMENTS 1
Quit
MAIN MENU
Quit
Yes
END       -     program ends
```

Thus, a fast, accurate and automatic method for evaluating follicular biopsy samples for the presence of comedones is provided. Further, the method of the present invention is safe and can be performed using readily available equipment and software from a variety of sources. The performance of the method itself is inexpensive and eliminates the need for harmful methods used upon humans and laboratory animals.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of evaluating skin samples taken from a human subject comprising the steps of:
    applying a film of adhesive to the skin of the subject;
    applying a microscopic slide to said adhesive and allowing said adhesive to set;
    removing said slide and said film with comedones and other materials of the skin attached thereto from the subject thereby yielding a skin specimen;
    placing said skin specimen under a compound microscope;
    subjecting said skin specimen to cross-polarized light;
    digitally scanning said skin specimen;
    digitally capturing and storing a binary image of said skin specimen;
    executing a computer program to evaluate said binary image;
    recording and storing data taken from said evaluation; and
    accessing said data using said computer program and thereafter performing an analysis of said skin specimen therewith for automatically evaluating the number of comedones contained in said skin specimen.

2. The method of claim 1 wherein said adhesive is a liquid polymerizable cyanoacrylate adhesive.

3. The method of claim 1 wherein said computer program evaluates said specimen by following a machine-readable task list comprising the steps of:
    applying a value to the ambient lighting upon the stage of said compound microscope;
    capturing an image of said specimen under said cross-polarized light;
    subtracting and filtering out image data that equals said value of ambient light;
    calculating the intensity of the pixels of irregular objects appearing on said specimen;
    calculating the mean average of the intensity of pixels neighboring said irregular object;
    substituting the pixels of said irregular object with the pixels of said mean average;
    assigning 64 grey video levels to said image whereby a zero level will appear as black and a level of 63 and above will appear as bright light;
    turning to an on state any pixels that appear in grey levels between level 50 and level 63;
    turning to an off state all pixels falling outside of grey levels between the levels of 50 and 63;
    deleting clusters of pixels in said image that are between 0 and 10 pixels in size, whereby only comedone-sized clusters remain in said image;
    measuring said comedone-sized clusters appearing in said image for size and shape; and
    counting the total number of comedone-sized clusters appearing in said image.

4. The method of claim 1 wherein said microscopic slide is glass.

5. The method of claim 1 wherein said compound microscope is set for a magnification of 15X.

6. The method of claim 1 wherein said method includes the prior step of applying a test substance to the skin of said human subject within at least one mapped test area.

7. The method of claim 1 wherein said compound microscope is a stereoscopic compound microscope.

8. A method of evaluating skin samples taken from a human subject comprising the steps of:
    applying a film of adhesive to the skin of the subject;
    applying a microscopic slide to said adhesive and allowing said adhesive to set;
    removing said slide and said film with comedones and other materials of the skin attached thereto from the subject thereby yielding a skin specimen;
    placing said skin specimen under a compound microscope;
    subjecting said skin specimen to cross-polarized light; and
    using image analysis hardware and software to evaluate said skin specimen and count the comedones thereon.

9. A method of evaluating skin samples taken from a human subject comprising the steps of:
    mapping at least one test area upon the skin of a live human subject using a marking device;
    applying a test substance to said test area;
    covering said test area with occlusive tape;
    allowing said test substance to remain on said test area for a predetermined period of time;
    removing said occlusive tape from said test area;
    applying a film of adhesive to said test area;
    applying a microscopic slide to said adhesive and allowing said adhesive to set;
    removing said slide and said film with comedones and other materials of said skin attached thereto from the subject thereby yielding a skin specimen;
    placing said skin specimen under a compound microscope;
    subjecting said skin specimen to cross-polarized light; and
    using image analysis hardware and software to evaluate said skin specimen and count said comedones thereon.

10. A method of evaluating skin samples taken from a human subject comprising the steps of:
    mapping at least one test area upon the skin of a live human subject using a marking device;
    applying a test substance to said test area;
    covering said test area with occlusive tape;
    allowing said test substance to remain on said test area for a predetermined period of time;
    removing said occlusive tape from said test area;
    applying a film of adhesive to said test area;
    applying a microscopic slide to said adhesive and allowing said adhesive to set;
    removing said slide and said film with comedones and other materials of said skin attached thereto from the subject thereby yielding a skin specimen;
    placing said skin specimen under a compound microscope;
    subjecting said skin specimen to cross-polarized light;
    digitally scanning said skin specimen;
    digitally capturing and storing a binary image of said skin specimen;
    executing a computer program to evaluate said binary image;
    recording and storing data taken from said evaluation; and
    accessing said data using said computer program and thereafter performing an analysis of said skin specimen therewith for automatically evaluating the number of said comedones contained in said skin specimen.

* * * * *